United States Patent

Cölln et al.

[11] Patent Number: 4,528,379
[45] Date of Patent: Jul. 9, 1985

[54] PREPARATION OF SUBSTITUTED THIADIAZOLYLOXYACETAMIDES

[75] Inventors: Reimer Cölln; Karl H. Mohrmann, both of Wuppertal, Fed. Rep. of Germany

[73] Assignee: Bayer Aktiengesellschaft, Leverkusen, Fed. Rep. of Germany

[21] Appl. No.: 515,084

[22] Filed: Jul. 18, 1983

[30] Foreign Application Priority Data

Jul. 28, 1982 [DE] Fed. Rep. of Germany ....... 3228132

[51] Int. Cl.³ ................ C07D 417/12; C07D 285/08; C07D 285/12
[52] U.S. Cl. .................... 546/209; 546/19; 546/164; 546/165; 544/111; 544/367; 548/129; 548/136
[58] Field of Search ............... 548/129, 136; 546/209, 546/19, 164, 165; 544/129, 136

[56] References Cited

U.S. PATENT DOCUMENTS 4,408,055 10/1983 Förster et al. ................... 548/129

FOREIGN PATENT DOCUMENTS 0018497 11/1980 European Pat. Off. ........... 548/136
0039811 11/1981 European Pat. Off. ........... 548/136
2914003 10/1980 Fed. Rep. of Germany .
3004326 8/1981 Fed. Rep. of Germany .
3038635 5/1982 Fed. Rep. of Germany ...... 548/136
3038636 5/1982 Fed. Rep. of Germany ...... 548/136

*Primary Examiner*—Robert T. Bond
*Attorney, Agent, or Firm*—Sprung Horn Kramer & Woods

[57] ABSTRACT

In a process for the preparation of a substituted thiadiazolyloxyacetamide of the formula

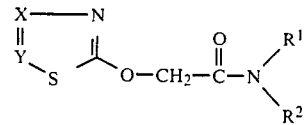

in which
$R^1$ and $R^2$ each independently is hydrogen, alkyl, alkenyl, alkenyl, alkinyl, optionally substituted cycloalkyl or cycloalkenyl, halogenoalkyl, alkoxyalkyl, alkoxy, aralkyl or optionally substituted aryl, or
$R^1$ and $R^2$, together with the nitrogen atom to which they are bonded, form an optionally substituted heterocyclic structure which can contain further hetero atoms,
One of X and Y is a nitrogen atom and the other a $C-R^3a$ grouping, and
$R^3$ is alkyl, alkoxy, alkylthio, alkylsulphonyl, halogenoalkyl, aralkyl, aralkoxy, aralkythio or optionally substituted aryl,
wherein a substituted 5-halogenothiadiazole of the formula

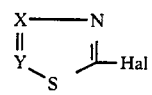

in which Hal is halogen,
is reacted with a hydroxyacetamide of the formula

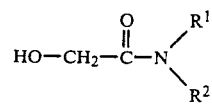

in the presence of a base as an acid acceptor and, optionally in the presence of a diluent, the improvement which comprises employing lithium hydroxide or its hydrate as the base, and carrying out the reaction at a temperature between about −10° C. and +60° C. The end products are known herbicides.

9 Claims, No Drawings

PREPARATION OF SUBSTITUTED THIADIAZOLYLOXYACETAMIDES

The invention relates to a new process for the preparation of known and new, herbicidally active, substituted thiadiazolyloxyacetamides.

It has already been disclosed that herbicidally active azolyloxycarboxamides are obtained when appropriate α-hydroxycarboxamides are reacted with appropriate halogenoazoles in the presence of an acid acceptor (see DE-OS (German Published Specification) No. 2,914,003 and DE-OS (German Published Specification) No. 3,004,326). Acid acceptors used hitherto were inorganic bases, such as, for example, sodium hydroxide, potassium hydroxide, potassium carbonate, potassium tert.-butylate or calcium oxide.

However, these acid acceptors are not completely suitable for the preparation of substituted thiadiazolyloxyacetamides, since, by promoting various side reactions, such as, for example, hydrolysis, N-alkylation and rearrangement, they lead to unsatisfactory yields and impure end products.

It has now been found that substituted thiadiazolyloxyacetamides of the general formula (I)

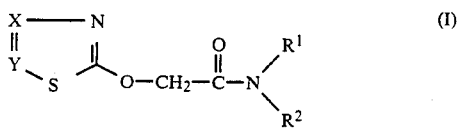

in which

R$^1$ and R$^2$ independently of one another represent hydrogen, alkyl, alkenyl, alkinyl, optionally substituted cycloalkyl or cycloalkenyl, halogenoalkyl, alkoxyalkyl and alkoxy, aralkyl and optionally substituted aryl, or R$^1$ and R$^2$, together with the nitrogen atom to which they are bonded, represent an optionally substituted, saturated or unsaturated heterocyclic structure which can contain further hetero atoms, and X and Y in each case alternately represent a nitrogen atom and the C-R$^3$ grouping, wherein R$^3$ represents alkyl, alkoxy, alkylthio, alkylsulphonyl, halogenoalkyl, aralkyl, aralkoxy, aralkylthio or optionally substituted aryl, are obtained in particularly good yields and high purity by reacting substituted 5-halogenothiadiazoles of the formula (II)

in which

X and Y have the meaning given above and

Hal represents halogen, with hydroxyacetamides of the formula (III)

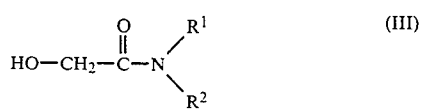

in which R$^1$ and R$^2$ have the meaning given above, in the presence of a base as an acid acceptor and, if appropriate, in the presence of a diluent, when lithium hydroxide or its hydrate is employed as the base, and the reaction is carried out at temperatures between −10° C. and +60° C.

It is extremely surprising that the use of lithium hydroxide as an acid-binding agent in the reaction according to the invention—in comparison to the previously known procedure—leads to considerably increased yields and to products of substantially improved purity, since in view of the prior art it was to be expected that the use of alkali metal hydroxides as acid-binding agents in the case of substituted thiadiazolyloxyacetamides would give only unsatisfactory yields and impure products (see DE-OS (German Published Specification) No. 3,004,326).

The process according to the invention preferably gives compounds of the formula (I) in which R$^1$ and R$^2$, independently of one another, represent hydrogen, straight-chain or branched alkyl having 1 to 8 carbon atoms, straight-chain or branched alkenyl and alkinyl, each having 2 to 8 carbon atoms, or cycloalkyl or cycloalkenyl, each having 3 to 7 carbon atoms and being optionally monosubstituted or polysubstituted by identical or different substituents, suitable substituents being, in particular, alkyl radicals having 1 to 4 carbon atoms, or represent straight-chain or branched alkoxy and alkoxyalkyl having 1 to 8 carbon atoms, halogenoalkyl having 1 to 8 carbon atoms and 1 to 5 halogen atoms, in particular fluorine, chlorine and bromine, aralkyl having 6 to 10 carbon atoms in the aryl part and 1 to 2 carbon atoms in the alkyl part, and aryl which has 6 to 10 carbon atoms and is optionally monosubstituted or polysubstituted by identical or different substituents, suitable substituents being: halogen, straight-chain or branched alkyl, alkoxy or alkylthio, each having 1 to 4 carbon atoms, halogenoalkyl, halogenoalkoxy and halogenoalkylthio, each having 1 to 2 carbon atoms and 1 to 5 halogen atoms, in particular fluorine, chlorine or bromine, and nitro, or R$^1$ and R$^2$, together with the nitrogen atom to which they are bonded, represent a saturated or unsaturated, 5-membered to 7-membered heterocyclic structure which is optionally monosubstituted or polysubstituted by identical or different substituents and can contain up to 2 further hetero atoms, in particular nitrogen and oxygen, suitable substituents being: straight-chain or branched alkyl having 1 to 6 carbon atoms, also in the form of a condensed ring system, aryl having 6 to 10 carbon atoms, also in the form of a condensed ring system, or dioxyalkylene having 2 to 3 carbon atoms, and X and Y have the meaning given in the definition of the invention, wherein R$^3$ preferably represents straight-chain or branched alkyl, alkoxy, alkylthio and alkylsulphonyl, each having 1 to 6 carbon atoms, halogenoalkyl having 1 to 6 carbon atoms and 1 to 5 halogen atoms, in particular fluorine, chlorine and bromine, aralkyl, aralkoxy and aralkylthio having 6 to 10 carbon atoms in the aryl part and 1 to 2 carbon atoms in the alkyl part, and aryl which has 6 to 10 carbon atoms and is optionally monosubstituted or polysubstituted by identical or different substituents, suitable substituents being: alkyl and alkoxy, each having 1 to 4 carbon atoms, halogenoalkyl having 1 to 4 carbon atoms and 1 to 5 halogen atoms, in particular fluorine, chlorine or bromine.

The process according to the invention particularly preferably relates to compounds of the formula (I) in which R¹ and R², independently of one another, represent hydrogen, straight-chain or branched alkyl having 1 to 6 carbon atoms, straight-chain or branched alkenyl and alkinyl, each having 2 to 6 carbon atoms, or cycloalkyl or cycloalkenyl, each of which has 5 to 7 carbon atoms and is optionally monosubstituted to trisubstituted by identical or different substituents from amongst methyl and ethyl, or represent branched or straight-chain alkoxy and alkoxyalkyl having 1 to 6 carbon atoms, halogenoalkyl having 1 to 6 carbon atoms and 1 to 5 halogen atoms, in particular fluorine, bromine and chlorine, benzyl, and phenyl which is optionally monosubstituted to trisubstituted by identical or different substituents, particularly preferred substituents being: methyl, ethyl, methoxy, methylthio, trifluoromethyl, trifluoromethoxy, trifluoromethylthio, fluorine, chlorine and nitro, or R¹ and R², together with the nitrogen atom to which they are bonded, represent the heterocyclic structures

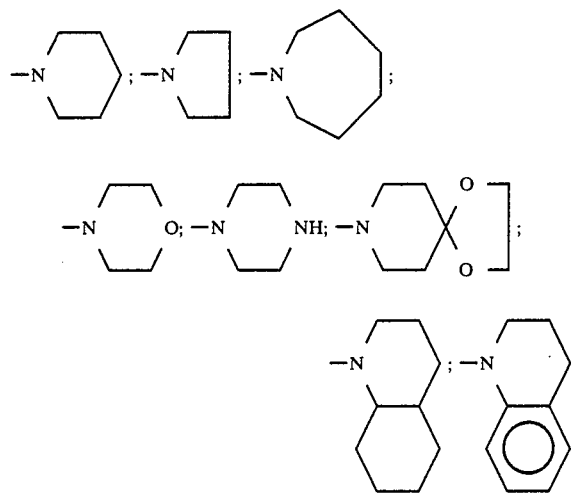

which are optionally monosubstituted to trisubstituted by identical or different substituents, particularly preferred substituents being: methyl, ethyl and phenyl, and X and Y have the meaning given in the definition of the invention, wherein R³ particularly preferably represents straight-chain or branched alkyl, alkoxy, alkylthio or alkylsulphonyl, each having 1 to 4 carbon atoms, halogenoalkyl having 1 to 2 carbon atoms and 1 to 5 identical or different halogen atoms, in particular fluorine, chlorine or bromine, benzyl or benzylthio, and represents phenyl which is optionally monosubstituted to trisubstituted by identical or different substituents, particularly preferred substituents being: methyl, methoxy and trifluoromethyl.

If, for example, 3-dichlorofluoromethyl-5-chloro-1,2,4-thiadiazole and hydroxyacetic acid N-methylanilide are used as starting materials, and 4-methylpentan-2-one is used as the solvent and lithium hydroxide hydrate is used as the acid-binding agent, the reaction taking place in the process according to the invention can be represented by the following equation:

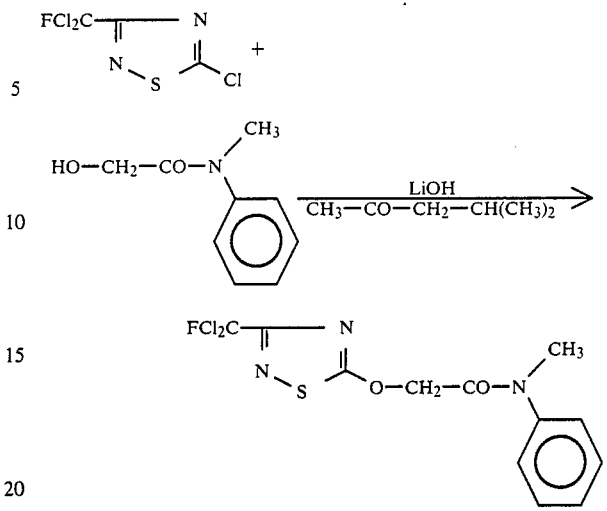

Formula (II) gives a general definition of the 5-halogenothiadiazoles to be used as starting materials in the process according to the invention. In this formula, X and Y preferably represent those radicals which in the description of the corresponding radicals in formula (I) have been stated to be preferred. Hal preferably represents fluorine, chlorine or bromine.

The following may be mentioned as examples of the starting compounds of the formula (II): 3-methyl-, 3-ethyl-, 3-n-propyl-, 3-isopropyl-, 3-t-butyl-, 3-dichlorofluoromethyl-, 3-difluorochloromethyl-, 3-trifluoromethyl-, 3-trichloromethyl-, 3-methylthio-, 3-benzylthio- and 3-methylsulphonyl-5-chloro-1,2,4,-thiadiazole, -5-bromo-1,2,4-thiadiazole and -5-fluoro-1,2,4,-thiadiazole, 2-methyl-, 2-ethyl-, 2-n-propyl-, 2-isopropyl-, 2-t-butyl-, 2-methylthio-, 2-ethylthio-, 2-n-propylthio-, 2-n-butylthio-, 2-methylsulphonyl-, 2-ethylsulphonyl-, 2-n-propylsulphonyl-, 2-phenyl-, 2-trifluoromethyl-, 2-trichloromethyl-, 2-difluorochloromethyl- and 2-dichlorofluoromethyl-5-chloro-1,3,4-thiadiazole, -5-bromo-1,3,4-thiadiazole and -5-fluoro-1,3,4-thiadiazole, 3-(3-trifluoromethyl-phenyl)- and 3-(4-trifluoromethyl-phenyl)-5-fluoro-, -5-chloro- and -5-bromo-1,2,4-thiadiazole, 2-phenyl-, 2-(2-trifluoromethylphenyl)-, 2-(3-trifluoromethylphenyl)-, 2-(4-trifluoromethylphenyl)-, 2-(2-methoxymethylphenyl)- and 2-(3-methoxymethylphenyl)-5-fluoro, -5-chloro- and -5-bromo-1,3,4-thiadiazole.

Compounds of the formula (II) are known, and can be prepared in a simple manner by processes which are in themselves known (see, for example, DE-OS (German Published Specification) No. 3,004,326; J. org. Chem. 27, 2589–2592 (1962); and U.S. Pat. No. 3,260,588).

Formula (III) gives a general definition of the hydroxyacetamides furthermore to be used as starting materials in the process according to the invention. In this formula, R¹ and R² preferably represent those radicals which in the description of the corresponding radicals in formula (I) have been stated to be preferred.

The following may be mentioned as examples of the starting compounds of the formula (III): hydroxyacetic acid methylamide, ethylamide, n-propylamide, isopropylamide, n-butylamide, iso-butylamide, dimethylamide, diethylamide, di-n-propylamide, di-iso-propylamide, di-n-butylamide, diisobutylamide, N-methyl-N-n-propylamide, N-methyl-N-n-butylamide, N-methyl-N- iso-propylamide, N-methyl-N-isobutylamide, N-methyl-N-t-butylamide, N-methyl-N-sec.-butyl-amide, N-ethyl-N-n-propylamide, N-ethyl-N-isopropylamide, N-ethyl-N-n-butylamide, N-ethyl-N-isobutylamide, N-ethyl-N-sec.-butylamide, N-ethyl-N-tert.-butylamide, N-n-propyl-N-iso-propylamide, N-n-propyl-N-n-butylamide, N-n-propyl-N-iso-butylamide, N-n-propyl-N-sec.-butylamide, N-n-propyl-N-tert.-butylamide, N-n-butyl-N-iso-butylamide, N-n-butyl-N-sec.-butylamide, N-n-butyl-N-tert.-butylamide, di-(2-methoxy-ethyl)-amide, di-allyl-amide, N-methyl-N-propargyl-amide, N-methyl-N-(1-methyl-propargyl)-amide, dipropargyl-amide, cyclopentyl-amide, N-methyl-N-cyclopentyl-amide, cyclohexyl-amide, N-methyl-N-cyclohexyl-amide, N-methyl-N-(1,1-dimethyl-propargyl)-amide, N-methyl-N-(2,2,2-trifluoro-ethyl)-amide, N-ethyl-N-cyclohexylamide, anilide, 2-nitro-, 3-nitro- and 4-nitro-phenyl-amide, 2-chloro-, 3-chloro- and 4-chloro-phenyl-amide, 2,4-dichloro-, 2,5-dichloro-, 3,4-dichloro- and 3,5-dichloro-phenyl-amide, 2-methyl-, 3-methyl- and 4-methyl-phenyl-amide, N-methylanilide, N-methyl-N-(2-nitro-phenyl)-, N-methyl-N-(3-nitro-phenyl)- and N-methyl-N-(4-nitro-phenyl)-amide, N-methyl-N-(2-chloro-phenyl)-, N-methyl-N-(3-chloro-phenyl)- and N-methyl-N-(4-chlorophenyl)-amide, N-methyl-N-(3-nitro-6-methyl-phenyl)-amide, N-methyl-N-(4-chloro-3-methyl-phenyl)-amide, N-methyl-N-(3,5-di-trifluoromethyl-phenyl)-amide, N-methyl-N-(4-methoxyphenyl)-amide, N-ethyl-anilide, N-ethyl-N-(2-nitro-phenyl)-, N-ethyl-N-(3-nitro-phenyl)- and N-ethyl-N-(4-nitro-phenyl)-amide, N-ethyl-N-(2-chloro-phenyl)-, N-ethyl-N-(3-chloro-phenyl)- and N-ethyl-N-(4-chloro-phenyl)-amide-, N-ethyl-N-(3-nitro-6-methyl-phenyl)-amide, N-propyl-anilide, N-propyl-N-(2-nitro-phenyl)-, N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chloro-phenyl)-amide, N-propyl-N-(2-methyl-phenyl)-, N-propyl-N-(3-methyl-phenyl)- and N-propyl-N-(4-methyl-phenyl)-amide, N-propyl-N-(3-nitro-6-methyl-phenyl)-amide, N-isopropylanilide, N-isopropyl-N-(2-methyl-phenyl)-, N-iso-propyl-N-(3-methyl-phenyl)- and N-iso-propyl-N-(4-methyl-phenyl)-amide, N-iso-propyl-N-(3-nitro-6-methyl-phenyl)-amide, N-butyl-anilide, N-butyl-N-(2-nitro-phenyl)-, N-butyl-N-(3-nitro-phenyl)- and N-butyl-N-(4-nitro-phenyl)-amide, N-butyl-N-(2-chlorophenyl)-, N-butyl-N-(3-chloro-phenyl)- and N-butyl-N-(4-chloro-phenyl)-amide, N-butyl-N-(2-methylphenyl)-, N-butyl-N-(3-methyl-phenyl)- and N-butyl-N-(4-methyl-phenyl)-amide, N-butyl-N-(3-nitro-6-methyl-phenyl)-amide, N-isobutyl-anilide, N-iso-butyl-N-(2-nitro-phenyl)-, N-iso-butyl-N-(3-nitro-phenyl)- and N-iso-butyl-N-(4-nitro-phenyl)-amide, N-iso-butyl-N-(2-chloro-phenyl)-, N-iso-butyl-N-(3-chloro-phenyl)- and N-iso-butyl-N-(4-chloro-phenyl)-amide, N-isobutyl-N-(2-methylphenyl)-, N-iso-butyl-N-(3-methyl-phenyl)- and N-iso-butyl-N-(4-methyl-phenyl)-amide, N-iso-butyl-N-(3-nitro-6-methyl-phenyl)-amide, benzylamide, dibenzylamide, N-methyl-N-benzylamide, N-ethyl-N-benzylamide, N-propyl-N-benzylamide, N-butyl-N-benzylamide, pyrrolidide, 2-methyl-pyrrolidide, morpholide, piperidide, 2-methyl-piperidide, 4-methyl-piperidide, 2,4-dimethyl-piperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6-ethyl-piperidide, 1,2,3,4-tetrahydroquinolide, 2-methyl-1,2,3,4-tetrahydroquinolide, perhydroquinolide, 2-methyl-perhydroquinolide, 3-methyl-piperidide, 3,5-dimethylpiperidide, 3,5-diethylpiperidide, N-methyl-N-(2-methylthiophenyl)-, N-methyl-N-(3-methylthiophenyl)- and N-methyl-N-(4-methylthiophenyl)-amide, N-methyl-N-(2-fluorophenyl)-, N-methyl-N-(3-fluorophenyl)- and N-methyl-N-(4-fluorophenyl)-amide, N-methyl-N-(2-trifluoromethylphenyl)-, N-methyl-N-(3-trifluoromethylphenyl)- and N-methyl-N-(4-trifluoromethylphenyl)-amide, N-methyl-N-(2-trifluoromethoxyphenyl)-, N-methyl-N-(3-trifluoromethoxyphenyl)- and N-methyl-N-(4-trifluoromethoxyphenyl)-amide, N-methyl-N-(2-trifluoromethylthiophenyl)-, N-methyl-N-(3-trifluoromethylthiophenyl)- and N-methyl-N-(4-trifluoromethylthiophenyl)-amide, N-methyl-N-methylenemethoxyamide, N-methyl-N-cyclohex-1-enylamide, N-methyl-N-(3,5,5-trimethylcyclohex-1-enyl)-amide, 6-methylperhydroquinolide, N-methyl-N-(2-methylphenyl)-, N-methyl-N-(3-methylphenyl)- and N-methyl-N-(4-methylphenyl)-amide, N-methyl-N-(2,3-dimethylphenyl)- and N-methyl-N-(2,4-dimethylphenyl)-amide, N-methyl-N-(2-methoxyphenyl)- and N-methyl-N-(3-methoxyphenyl)-amide, N-methyl-N-(2,4-dichlorophenyl)- and N-methyl-N-(3,4-dichlorophenyl)-amide, N-ethyl-N-(2-methylphenyl)-, N-ethyl-N-(3-methyl-phenyl)- and N-ethyl-N-(4-methylphenyl)-amide, N-benzyl-anilide, N-benzyl-N-propyl-amide, N-ethyl-N-(2,2,2-trifluoroethyl)-amide, N,N-di-(2-methoxyethyl)-amide, N-methoxy-N-butylamide, N-methyl-N-(2-methyl-perhydrofuran-2-yl)-methyl-amide, perhydroazepide, 3-ethyl-piperidide, 4-phenyl-1,4-piperazide, 3,3,5-trimethyl-perhydroazepide, 4,4-dioxyethylenepiperidide, 3-methyl-morpholide and 3,5-dimethylmorpholide.

Compounds of the formula (III) are known and can be prepared in a simple manner by processes which are in themselves known. (See, for example, DE-OS (German Published Specification) No. 3,004,326; European Pat. No. 5,501; DE-OS (German Published Specification) No. 2,904,490; U.S. Pat. No. 3,399,988; DE-OS (German Published Specification) No. 2,201,432; and DE-OS (German Published Specification) No. 2,647,481).

The process according to the invention is preferably carried out in the presence of a suitable diluent. Suitable diluents are virtually all inert organic solvents. These include, in particular, alcohols, such as methanol, ethanol, n- and iso-propanol, n-, iso-, sec.- and tert.-butanol, ethers, such as diethyl ether, dibutyl ether, tetrahydrofuran and dioxane, ketones, such as acetone, methyl ethyl ketone, methyl isopropyl ketone and methyl isobutyl ketone, nitriles, such as acetonitrile and propionitrile, and the highly polar solvents dimethylformamide, dimethylsulphoxide, sulpholane and hexamethylphosphoric acid triamide.

In the process according to the invention, the reaction temperature is kept in general between −10° C. and +60° C., preferably between +20° C. and +40° C. The process is carried out in general under atmospheric pressure.

To carry out the process according to the invention, 0.9 to 1.2 mols of hydroxyacetamide of the formula (III) and 0.9 to 1.2 mols of lithium hydroxide or its hydrate are employed per mol of 5-halogenothiadiazole of the formula (II). Preferably, equimolar amounts of all three components are used.

In a preferred embodiment of the process according to the invention, the starting compounds of the formulae (II) and (III), dissolved in a solvent, are initially introduced, and the lithium hydroxide or its hydrate is added in portions. An alternative embodiment comprises initially introducing the hydroxyacetamide of the formula (III) together with the lithium hydroxide or its hydrate in the appropriate solvent, and adding the thiadiazole component of the formula (II) in portions.

In both embodiments, the reaction mixture is then stirred at the preferred reaction temperature until the reaction is complete, and then worked up in the customary manner.

The known compounds of the formula (I) which are to be prepared by the process according to the invention are known to possess herbicidal properties (see, for example, DE-OS (German Published Specification) No. 3,004,326); the new compounds obtainable by the method described here have principally the same action.

EXAMPLE 1

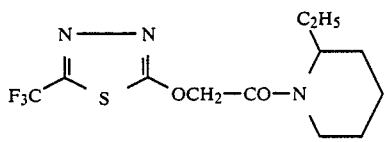

171.2 g (1 mole) of hydroxyacetic acid 2-ethyl-piperidide and 188.6 g (1 mol) of 2-trifluoromethyl-5-chloro-1,3,4-thiadiazole, dissolved in 800 ml of methyl isobutyl ketone, are initially introduced, and 43.5 g (1 mol) of lithium hydroxide hydrate are added in portions in the course of 30 to 45 minutes, at 20°–25° C., while stirring. The mixture is stirred for a further hour at 20°–25° C.

A further 200 ml of the solvent and 1 liter of water are then added, and the phases are separated. The organic phase is washed neutral, and freed from solvent under reduced pressure, at a maximum bath temperature of 40° C. 288.9 g (89.4% of theory) of 2-trifluoromethyl-1,3,4-thiadiazol-5-yl-oxyacetic acid 2-ethyl-piperidide are obtained in the form of a clear pale yellow oil of refractive index $n^{20}=1.4867$. According to analysis (HPLC), the reaction product has a purity of 85%.

EXAMPLE 2

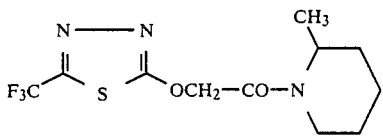

157.2 g (1 mol) of hydroxyacetic acid 2-methyl-piperidide and 188.6 g (1 mol) of 2-trifluoromethyl-5-chloro-1,3,4-thiadiazole, dissolved in 800 ml of methyl isobutyl ketone, are initially introduced, and 43.5 g (1 mol) of lithium hydroxide hydrate are added in portions in the course of approximately 45 minutes, at 20°–25° C., while stirring.

The mixture is stirred for a further hour at 20°–25° C. A further 200 ml of the solvent and 1 liter of water are then added, the mixture is stirred and the phases are separated.

The organic phase is washed neutral, and is freed from solvent under reduced pressure, at a maximum bath temperature of 40° C. 275.4 g (89% of theory) of 2-trifluoromethyl-1,3,4-thiadiazol-5-yl-oxyacetic acid 2-methylpiperidide are obtained in the form of an orange-colored oil of refractive index $n^{20}=1.4803$.

EXAMPLE 3

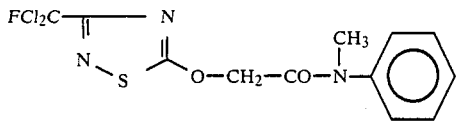

4.4 g of lithium hydroxide hydrate (0.1 mol) are added in portions in the course of 30 minutes, at 25°–30° C., to 16.5 g (0.1 mol) of hydroxyacetic acid N-methylanilide and 16.6 g (0.075 mol) of 3-dichlorofluoromethyl-5-chloro-1,2,4-thiadiazole in 80 ml of methyl isobutyl ketone, and the mixture is stirred for a further 2½ hours at 20°–25° C.

The organic phase is then washed neutral, and the solvent is removed under reduced pressure, at a maximum bath temperature of 50° C. The residue which crystallizes on cooling is recrystallized from 30 ml of ligroin. 24.3 g (92.5% of theory) of 3-dichlorofluoromethyl-1,2,4-thiadiazol-5-yl-oxyacetic acid N-methylanilide are obtained in the form of colorless crystals of melting point 71°–73° C.

EXAMPLE 4

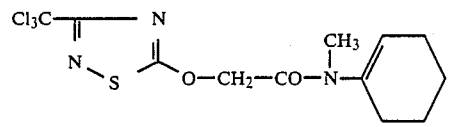

3.1 g (0.07 mol) of lithium hydroxide hydrate are added in portions, at 0° C., to 16.7 g (0.07 mol) of 3-trichloromethyl-5-chloro-1,2,4-thiadiazole and 11.8 g (0.07 mol) of hydroxyacetic acid N-methyl-N-cyclohex-1-enylamide in 100 ml of methyl isobutyl ketone, and the mixture is stirred for 30 minutes at 0° C. and then overnight at 25° C. After water has been added, the reaction product which separates out as a solid is filtered off under suction, washed and dried. 22.0 g (84.8% of theory) of 3-trichloromethyl-1,2,4-thiadiazol-5-yl-oxyacetic acid N-methyl-N-cyclohexen-1-yl-amide are obtained in the form of beige-colored crystals of melting point 78° C.

COMPARATIVE EXAMPLE A (Use of NaOH)

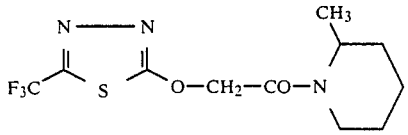

15.7 g (0.1 mol) of hydroxyacetic acid 2-methyl-piperidide and 18.9 g (0.1 mol) of 2-trifluoromethyl-5-chloro-1,3,4-thiadiazole, dissolved in 80 ml of methyl isobutyl ketone, are initially introduced, and 4.5 g of sodium hydroxide in the form of flakes are added in portions in the course of 20 minutes, at 20°–25° C., while stirring, and the mixture is stirred for a further hour at 20°–25° C.

A further 20 ml of the solvent and 100 ml of water are added, and the phases are separated. The organic phase is washed neutral, and is freed from solvent under reduced pressure at a maximum bath temperature of 40° C. 25.0 g of a dark viscous oil are obtained, which according to analysis (HPLC), however, contains only 62.7% of 2-trifluoromethyl-1,3,4-thiadiazol-5-yl-oxyacetic acid 2-methylpiperidide.

COMPARATIVE EXAMPLE B (Use of NaOH)

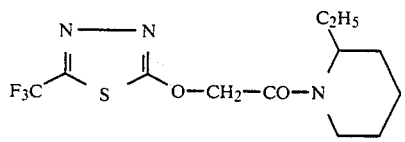

17.1 g (0.1 mol) of hydroxyacetic acid 2-ethylpiperidide and 18.9 g (0.1 mol) of 2-trifluoromethyl-5-chloro-1,3,4-thiadiazole, dissolved in 80 ml of methyl isobutyl ketone, are initially introduced, and 4.5 g of sodium hydroxide in the form of flakes are added in portions in the course of 20 minutes, at 20° to 25° C., while stirring, and the mixture is stirred for a further hour at 20° to 25° C.

A further 20 ml of the solvent and 100 ml of water are added, and the phases are separated. The organic phase is washed neutral, and is freed from solvent under reduced pressure at a maximum bath temperature of 40° C. 26.7 g of a dark oil are obtained, which according to analysis (HPLC), however, contains only 62.6% of 2-trifluoromethyl-1,3,4-thiadiazol-5-yl-oxyacetic acid 2-ethylpiperidide.

It will be appreciated that the instant specification and examples are set forth by way of illustration and not limitation, and that various modifications and changes may be made without departing from the spirit and scope of the present invention.

What is claimed is:

1. In a process for the preparation of a substituted thiadiazolyloxyacetamide of the formula

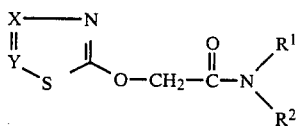

in which $R^1$ and $R^2$ each independently is hydrogen, alkyl, alkenyl, alkenyl, alkinyl, optionally substituted cycloalkyl or cycloalkenyl, halogenoalkyl, alkoxyalkyl, alkoxy, aralkyl or optionally substituted aryl, or $R^1$ and $R^2$, together with the nitrogen atom to which they are bonded, form a heterocyclic structure of the formula

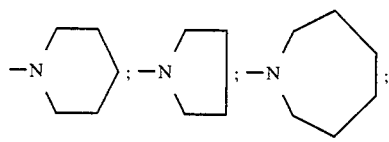

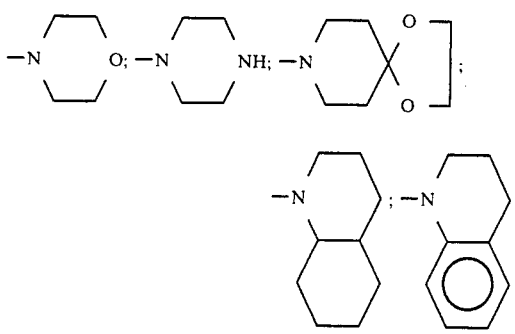

which is optionally substituted by alkyl having up to 6 carbon atoms, aryl having 6 to 10 carbon atoms and/or dioxyalkylene having 2 or 3 carbon atoms, one of X and Y is a nitrogen atom and the other a C-$R^3$ a grouping, and $R^3$ is alkyl, alkoxy, alkylthio, alkylsulphonyl, halogenoalkyl, aralkyl, aralkoxy, aralkythio or optionally substituted aryl, wherein a substituted 5-halogenothiadiazole of the formula

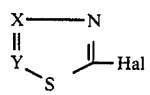

in which Hal is halogen, is reacted with a hydroxyacetamide of the formula

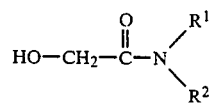

in the presence of a base as an acid acceptor and, optionally in the presence of a diluent, the improvement which comprises employing lithium hydroxide or its hydrate as the base, and carrying out the reaction at a temperature between about −10° C. and +60° C.

2. A process according to claim 1, wherein the reaction is carried out at a temperature between about +20° C. and +40° C.

3. A process according to claim 1, wherein about 0.9 to 1.2 mols of hydroxyacetamide and about 0.9 to 1.2 mols of lithium hydroxide or its hydrate are employed per mol of 5-halogenothiadiazole.

4. A process according to claim 1, wherein the 5-halogenothiadiazole is 2-trifluoromethyl-5-chloro-1,3,4-thiadiazole and the hydroxy acetamide is hydroxyacetic acid 2-ethylpiperidide.

5. A process according to claim 1, wherein the 5-halogenothiadiazole is 2-trifluoromethyl-5-chloro-1,3,4-thiadiazole and the hydroxy acetamide is hydroxyacetic acid 2-methylpiperidide.

6. A process according to claim 1, wherein the 5-halogenothiadiazole is 3-dichlorofluoromethyl-5-chloro-1,2,4-thiadiazole and the hydroxy acetamide is hydroxyacetic acid N-methyl-anilide.

7. A process according to claim 1, wherein the 5-halogenothiadiazole is 3-trifluoromethyl-5-chloro-1,2,4-thiadiazole and the hydroxy acetamide is hydroxyacetic acid N-methyl-N-cyclohex-1-enylamide.

8. A process according to claim 1, wherein $R^1$ and $R^2$ each independently is hydrogen, alkyl, alkenyl or alkinyl each having up to 8 carbon atoms, cycloalkyl or cycloalkenyl each having up to 7 carbon atoms and optionally substituted by alkyl of up to 4 carbon atoms, alkoxy or alkoxyalkyl each having up to 8 carbon atoms, halogenoalkyl having up to 8 carbon atoms and up to 5 halogen atoms, aralkyl having 6 to 10 carbon atoms in the aryl moiety and 1 or 2 carbon atoms in the alkyl moiety, or aryl which has 6 to 10 carbon atoms and is optionally substituted by alkyl, alkoxy or alkylthio each having up to 4 carbon atoms, halogenalkyl, halogenoalkoxy or halogenoalkylthio each having 1 or 2 carbon atoms and 1 to 5 halogen atoms, halogen and/or nitro, or $R^1$ and $R^2$, together with the nitrogen atom to which they are bonded, form a heterocyclic structure of the formula

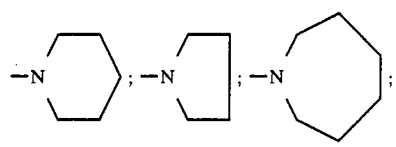

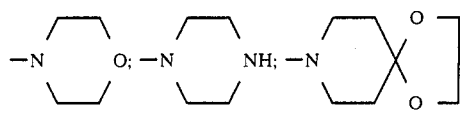

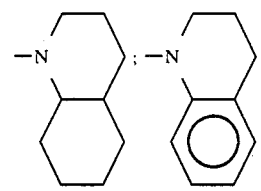

which is optionally substituted by alkyl having up to 6 carbon atoms, aryl having 6 to 10 carbon atoms and/or dioxyalkylene having 2 or 3 carbon atoms, and $R^3$ is alkyl, alkoxy, alkylthio or alkylsulphonyl each having up to 6 carbon atoms, halogenoalkyl having up to 6 carbon atoms and up to 5 halogen atoms, aralkyl, aralkoxy or aralkylthio having 6 to 10 carbon atoms in the aryl moiety and 1 or 2 carbon atoms in the alkyl moiety, or aryl having 6 to 10 carbon atoms and optionally substituted by alkyl or alkoxy having up to 4 carbon atoms, or halogenoalkyl having up to 4 carbon atoms and up to 5 halogen atoms.

9. A process according to claim 3, wherein the reaction is carried out at a temperature between about $+20°$ C. and $+40°$ C. and $R^1$ and $R^2$ each independently is hydrogen, alkyl, alkenyl or alkinyl having up to 6 carbon atoms, cycloalkyl or cycloalkenyl.

* * * * *